(12) United States Patent
Tegels

(10) Patent No.: US 8,974,476 B2
(45) Date of Patent: Mar. 10, 2015

(54) VASCULAR CLOSURE DEVICE WITH COMPACTION TUBE SUTURE CUTTING PORT AND METHODS

(75) Inventor: Zachary J. Tegels, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 281 days.

(21) Appl. No.: 13/426,465

(22) Filed: Mar. 21, 2012

(65) Prior Publication Data
US 2012/0245597 A1 Sep. 27, 2012

Related U.S. Application Data

(60) Provisional application No. 61/466,844, filed on Mar. 23, 2011.

(51) Int. Cl.
- A61B 17/04 (2006.01)
- A61B 17/00 (2006.01)
- A61B 17/22 (2006.01)
- A61B 17/29 (2006.01)

(52) U.S. Cl.
CPC ......... *A61B 17/0057* (2013.01); *A61B 17/0467* (2013.01); *A61B 2017/00526* (2013.01); *A61B 2017/00654* (2013.01); *A61B 2017/00659* (2013.01); *A61B 2017/00663* (2013.01); *A61B 2017/22072* (2013.01); *A61B 2017/2905* (2013.01)
USPC ............................ 606/148; 606/144; 606/213

(58) Field of Classification Search
CPC ................................................ A61B 17/0467
USPC ......... 606/213, 214, 215, 139, 144–150, 232; 623/23.72
See application file for complete search history.

(56) References Cited

U.S. PATENT DOCUMENTS

| | | | | |
|---|---|---|---|---|
| 3,995,619 | A * | 12/1976 | Glatzer | 600/550 |
| 6,045,569 | A | 4/2000 | Kensey et al. | |
| 6,090,130 | A | 7/2000 | Nash et al. | |
| 6,179,863 | B1 * | 1/2001 | Kensey et al. | 606/215 |
| 7,008,439 | B1 * | 3/2006 | Janzen et al. | 606/213 |
| 7,250,057 | B2 | 7/2007 | Forsberg | |
| 7,435,251 | B2 * | 10/2008 | Green | 606/232 |
| 7,618,436 | B2 | 11/2009 | Forsberg | |
| 7,618,438 | B2 | 11/2009 | White et al. | |
| 7,749,247 | B2 | 7/2010 | Tegg | |
| 7,749,248 | B2 | 7/2010 | White et al. | |
| 7,931,670 | B2 | 4/2011 | Fiehler et al. | |
| 8,211,123 | B2 * | 7/2012 | Gross et al. | 606/148 |
| 8,226,666 | B2 * | 7/2012 | Zarbatany et al. | 606/139 |
| 8,398,680 | B2 * | 3/2013 | Sauer et al. | 606/232 |
| 2002/0087178 | A1 * | 7/2002 | Nobles et al. | 606/167 |
| 2003/0109891 | A1 * | 6/2003 | Dana et al. | 606/148 |
| 2004/0097865 | A1 * | 5/2004 | Anderson et al. | 604/22 |
| 2006/0047314 | A1 * | 3/2006 | Green | 606/232 |
| 2006/0178682 | A1 * | 8/2006 | Boehlke | 606/148 |

(Continued)

*Primary Examiner* — Katrina Stransky
(74) *Attorney, Agent, or Firm* — Holland & Hart

(57) ABSTRACT

A tissue puncture closure device includes an anchor, a sealing plug, a compaction member, a suture, and a suture cutting member. The compaction member is configured to compress the sealing plug toward the anchor. The suture is coupled to the sealing plug and anchor, and a portion of the suture extends through at least a portion of the compaction member. The suture cutting member extends through an aperture in a sidewall of the compaction member and is operable to cut the suture at a location within the compaction member.

18 Claims, 14 Drawing Sheets

(56) References Cited

U.S. PATENT DOCUMENTS

| | | |
|---|---|---|
| 2007/0005081 A1* | 1/2007 | Findlay et al. ............... 606/148 |
| 2008/0086152 A1* | 4/2008 | McKay et al. ............... 606/139 |
| 2008/0228165 A1* | 9/2008 | Spence et al. ............... 604/510 |
| 2011/0100173 A1* | 5/2011 | Stone et al. ............... 83/13 |
| 2011/0251641 A1* | 10/2011 | Sauer et al. ............... 606/230 |

* cited by examiner

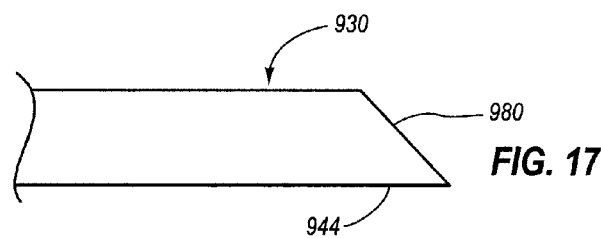
FIG. 17
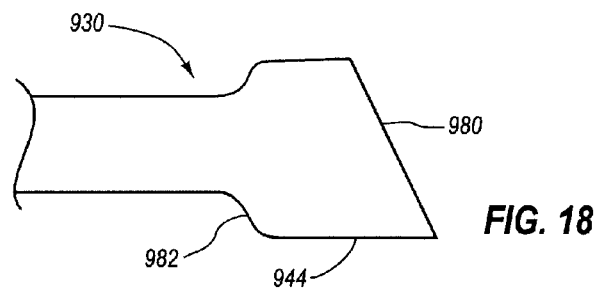
FIG. 18
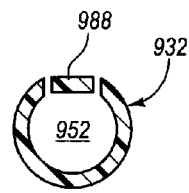
FIG. 22
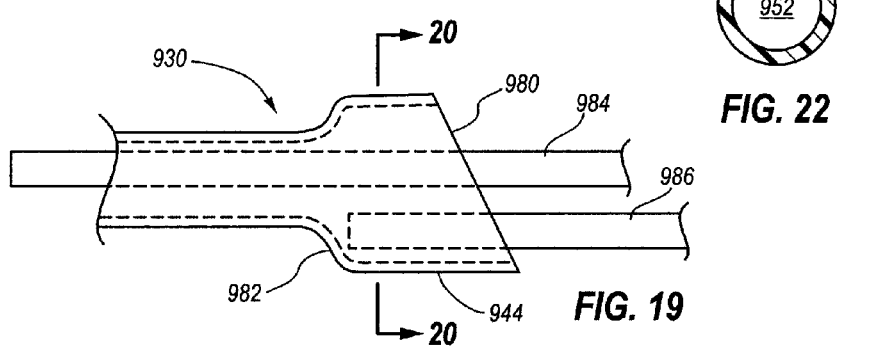
FIG. 19
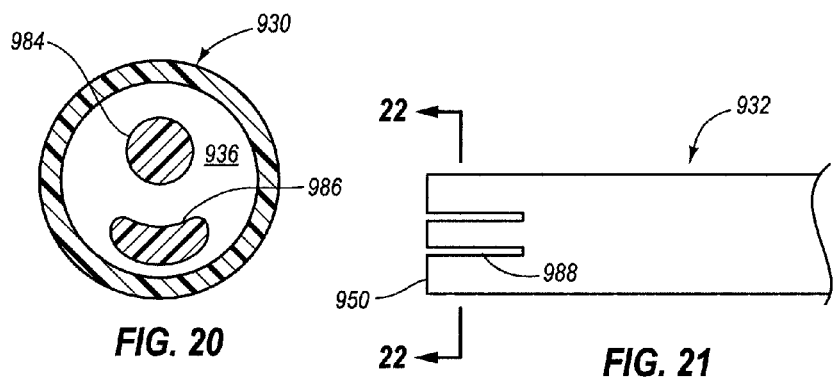
FIG. 20
FIG. 21

VASCULAR CLOSURE DEVICE WITH COMPACTION TUBE SUTURE CUTTING PORT AND METHODS

CROSS-REFERENCE TO RELATED APPLICATION

This application claims the benefit of the filing date of U.S. Provisional Application No. 61/466,844, filed 23 Mar. 2011, and entitled VASCULAR CLOSURE DEVICE WITH COMPACTION TUBE SUTURE CUTTING PORT AND METHODS, the disclosure of which is hereby incorporated in its entirety by this reference.

TECHNICAL FIELD

The present disclosure relates generally to vascular closure devices, and more particularly to suture cutting features for vascular closure devices.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

Prior closure devices, such as the ones described in the above-mentioned patents, place a sealing plug at the tissue puncture site. Deployment of the sealing plug involves ejecting the plug from within a device sheath and compacting the plug down to an outer surface of the tissue puncture using a compaction member. After the sealing plug has been compacted, the suture is manually cut by the operator at a location outside of the patient. There is a need for improving the mechanism and method for cutting a suture of the closure device after compacting the sealing plug with a compaction member.

SUMMARY

One aspect of the present disclosure relates to a tissue puncture closure device that includes an anchor, a sealing plug, a compaction member, a suture, and a suture cutting member. The compaction member is configured to move the sealing plug toward the anchor. The compaction member includes a sidewall and an aperture defined in the sidewall. The suture is coupled to the sealing plug and anchor, and a portion of the suture extends through at least a portion of the compaction member and out of the aperture. The suture cutting member extends through the aperture and is operable to cut the suture within the compaction member.

The suture cutting member may be operable to cut the suture at a location distal of the aperture. The suture cutting member may be configured to cut the suture at a location within a percutaneous incision of a patient. The suture cutting member may be constructed as, for example, a lancet, a needle, a heat cutting member, or a rotational cutting member. The compaction member may include a distal portion that includes the aperture, and a proximal portion coupled to a proximal end of the distal portion. The proximal portion may have a greater flexibility than the distal portion. The compaction member may further include a connector configured to connect the distal portion to the proximal portion. A first portion of the connector may be insertable into the distal portion and a second portion of the connector may be insertable into the proximal portion. The compaction member may have a greater maximum outer dimension at a location distal of the aperture than a maximum outer dimension of the compaction member proximal of the aperture.

Another aspect of the present disclosure relates to a suture cutting assembly that is adapted for use with a tissue puncture closure device. The suture cutting assembly includes a sealing pad, a compaction member, a suture, and a suture cutting member. The compaction member may have an aperture defined in a sidewall thereof, wherein the compaction member is configured to compress the sealing pad. The suture may be coupled to the sealing pad. The suture cutting member may be adapted to extend through the aperture and cut the suture at a location within the compaction member.

The compaction member may include a distal compaction portion having the aperture defined therein, and a proximal compaction portion connected to the distal compaction portion. The proximal compaction portion may have a greater flexibility than the distal compaction portion. The suture cutting assembly may further comprise a connector configured to connect the distal and proximal compaction portions together at a location proximal of the aperture. The aperture may be arranged facing in an axial direction and positioned at a location between proximal and distal ends of the compaction member.

A further aspect of the present disclosure relates to a method of sealing a tissue puncture in an internal tissue wall that is accessible through a percutaneous incision. The method may include providing a tissue puncture closure device having an anchor, a sealing plug, a suture coupled to the anchor and the sealing plug, a compaction member, and a suture cutting device. The compaction member may include an aperture defined in a sidewall thereof. The method may further include inserting the tissue puncture closure device into the percutaneous incision, advancing the anchor through the tissue puncture, compressing the sealing member within the percutaneous incision, and extending the suture cutting device through the aperture to cut the suture at a location within the percutaneous incision.

The compaction member may include a distal portion and a proximal portion having different flexibility properties, and cutting the suture includes moving the suture cutting member within the distal portion. The method may include extending the suture out of the aperture prior to cutting the suture. The tissue puncture closure device may include a carrier tube within which the sealing plug and compaction member are positioned. Inserting the tissue puncture closure device may include inserting a distal end of the carrier tube into the percutaneous incision. The method may further comprise retracting the carrier tube after advancing the anchor through the tissue puncture and prior to compacting the sealing member within the percutaneous incision.

Another aspect of the present disclosure relates to a method of manufacturing a sealing pad compaction member of a tissue puncture closure device. The method includes providing a compaction member assembly that includes a distal portion having a flared proximal end and defining a distal lumen, and a proximal portion having a pair of axially arranged slits extending proximally from a distal end of the proximal portion to define a tab member. The proximal portion may define a proximal lumen. The method further includes inserting a first mandrel through the distal portion, wherein the first mandrel has a proximal end that extends proximal of the flared proximal end, and inserting a second mandrel through the proximal portion, wherein the second mandrel has a distal end that extends distal of the distal end of the proximal portion. The method may also include positioning the tab member and a distal end of the second mandrel within the flared proximal end of the distal portion, applying heat to the compaction assembly to create a thermal bond between the distal and proximal portions, and removing the first and second mandrels from the compaction member.

The compaction member assembly may provide flow communication between the distal and proximal lumens and an aperture defined in a sidewall of the compaction member. The method may also include providing a heat shrink member and positioning the heat shrink member over the compaction member after the step of positioning the tab member and before the step of applying heat.

Additional advantages and novel features will be set forth in the description which follows or may be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not intend to be limiting.

FIG. 17 is a side view of a first portion of another example compaction member assembly in accordance with the present disclosure.

FIG. 18 is a side view of the first portion of FIG. 17 with a flared proximal end.

FIG. 19 is a side view of the first portion of FIG. 18 with a pair of mandrels inserted therein.

FIG. 20 is a cross-sectional view of the assembly of FIG. 19.

FIG. 21 is a side view of a second portion of the compaction member assembly of FIG. 17.

FIG. 22 is a cross-sectional view of the second portion of FIG. 21.

Throughout the drawings, identical reference numbers designate similar, but not necessarily identical, elements.

DETAILED DESCRIPTION

Figure 1:
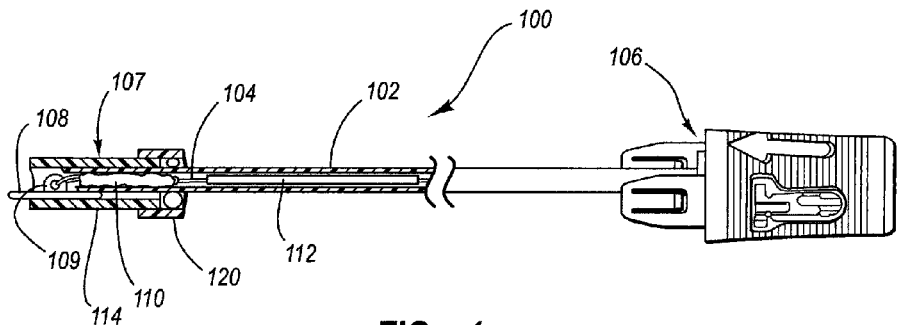
FIG. 1 is a perspective view of an example vascular closure device according to the prior art.

As mentioned above, vascular procedures are conducted throughout the world and require access to an artery through a puncture. Often, the artery is a femoral artery. To close the puncture following completion of the procedure, many times a closure device is used to sandwich the puncture between an anchor and a sealing plug. A suture is often used to couple together the anchor and sealing plug. A force may be applied along the suture to draw the anchor and sealing plug toward each other as the sealing plug is compressed against the puncture. Typically, the suture is manually cut at a location outside of the patient after confirmation that the puncture has been sealed. Cutting the suture releases the anchor and sealing plug from the remaining portions of the closure device. Leaving a length of suture protruding through the patient's skin surface may result in complications such as, for example, infections that may arise where the suture exits the patient's skin. Further, requiring the extra step of manually cutting the suture with an instrument that is separate from the closure device requires additional time and adds complexity to the procedure.

The present disclosure describes methods and apparatus that facilitate cutting of the suture using features that are integral with the closure device. The present disclosure further describes methods and apparatuses that facilitate cutting of the suture within a percutaneous incision at a location below the patient's outer skin surface. While the vascular instruments shown and described below include procedure sheaths and puncture sealing devices, the application of principles described herein is not limited to the specific devices shown. The principles described herein may be used with any medical device. Therefore, while the description below is directed primarily to vascular procedures and certain embodiments of a vascular closure device, the methods and apparatus are only limited by the appended claims.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engagable" are also used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-5, a vascular puncture closure device 100 is shown according to the prior art. Some example closure devices are disclosed in U.S. Pat. Nos. 7,931,670, 7,618,438, and 7,618,436, which are hereby incorporated in their entireties by this reference. The vascular puncture closure device 100 includes a carrier tube 102 with a filament or suture 104 extending at least partially therethrough. The vascular puncture closure device 100 also includes a first or proximal end 106 and a second or distal end 107. An anchor 108 is positioned external to the second or distal end 107 of the carrier tube 102. The anchor may be an elongated, stiff, low profile member having an eye 109 formed at the middle. The anchor 108 is typically made of a biologically resorbable polymer.

The suture 104 is threaded through the anchor 108 and back to a collagen pad 110 (also referred to herein as a sealing plug 110). The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the vascular puncture closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
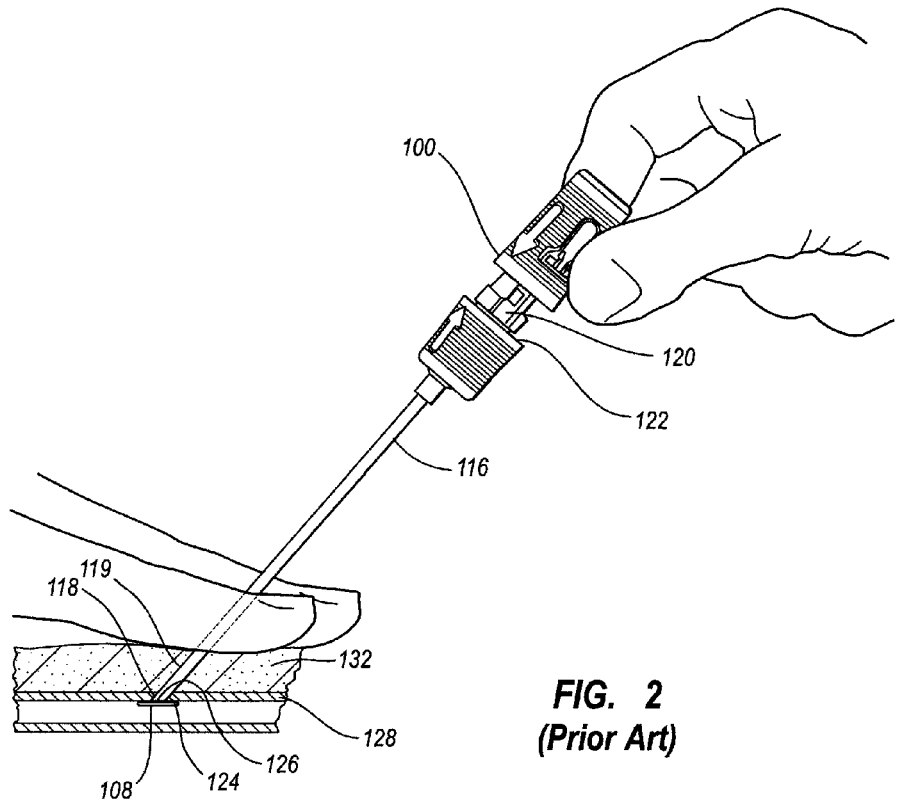
FIG. 2 is a perspective view of the vascular closure device shown in FIG. 1 with an anchor disposed in a vessel.
Figure 3:
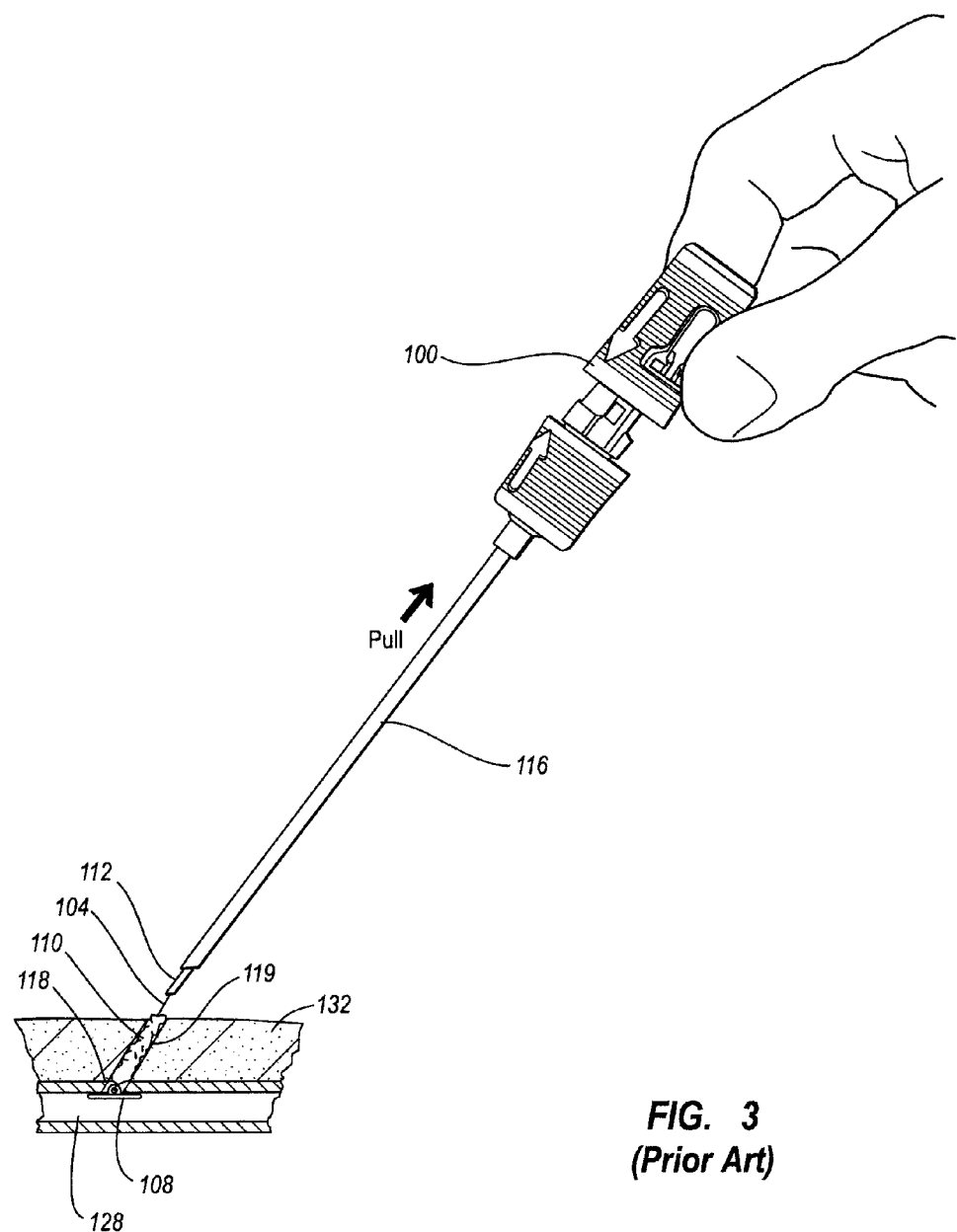
FIG. 3 is a perspective view of the vascular closure device shown in FIG. 1 with a sealing pad disposed in the percutaneous incision.
Figure 4:
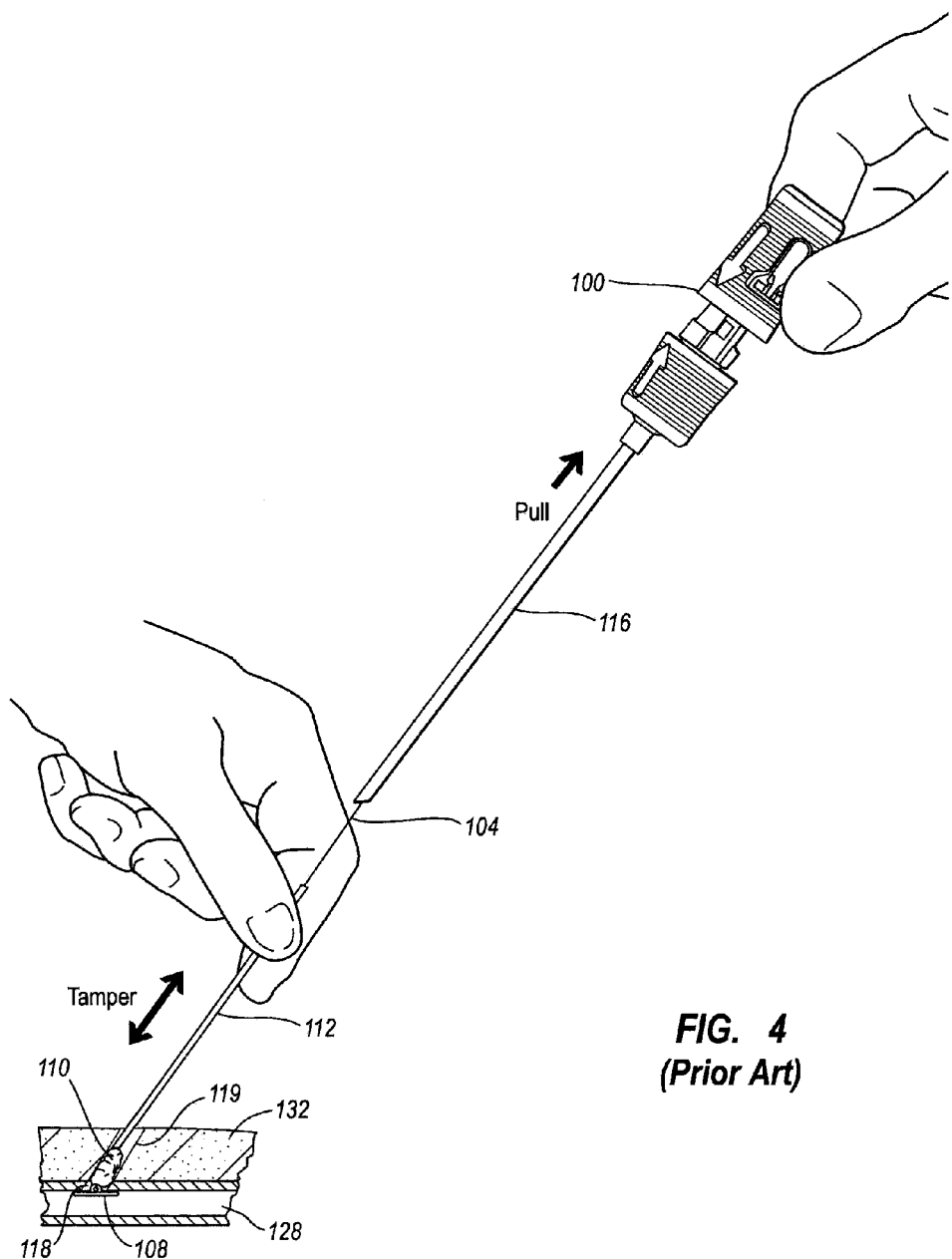
FIG. 4 is a perspective view of the vascular closure device shown in FIG. 1 with the sealing pad being compacted by a compaction member.

The flush arrangement of the anchor 108 and carrier tube 102 allows the anchor 108 to be inserted into a procedure sheath such as insertion sheath 116 as shown in FIGS. 2-4, and eventually through an arterial puncture 118. The insertion sheath 116 is shown in FIGS. 2-4 inserted through a percutaneous incision 119 of a tissue layer 132 and into an artery 128. However, the bypass tube 114 (see FIG. 1) includes an oversized head 120 that prevents the bypass tube 114 from passing through an internal passage of the insertion sheath 116. Therefore, as the vascular puncture closure device 100 is inserted into the insertion sheath 116, the oversized head 120 bears against a surface 122 of insertion sheath 116.

Further insertion of the vascular puncture closure device 100 results in sliding movement between the carrier tube 102 and the bypass tube 114, and releases the anchor 108 from the bypass tube 114. However, the anchor 108 remains in the flush arrangement shown in FIG. 1 following release from the bypass tube 114, limited in movement by the insertion sheath 116.

The insertion sheath 116 may include a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the vascular puncture closure device 100 and the insertion sheath 116 are withdrawn together, ejecting the collagen pad 110 from the carrier tube 102 into the percutaneous incision 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 104. Thus, the tissue puncture is sandwiched between the anchor 108 and the collagen pad 110, thereby sealing the arterial puncture 118. The suture 104 is then cut and the percutaneous incision 119 may be closed. The suture 104, anchor 108, and collagen pad 110 are generally made of resorbable materials and therefore remain in place while the arterial puncture 118 heals.

Figure 5:
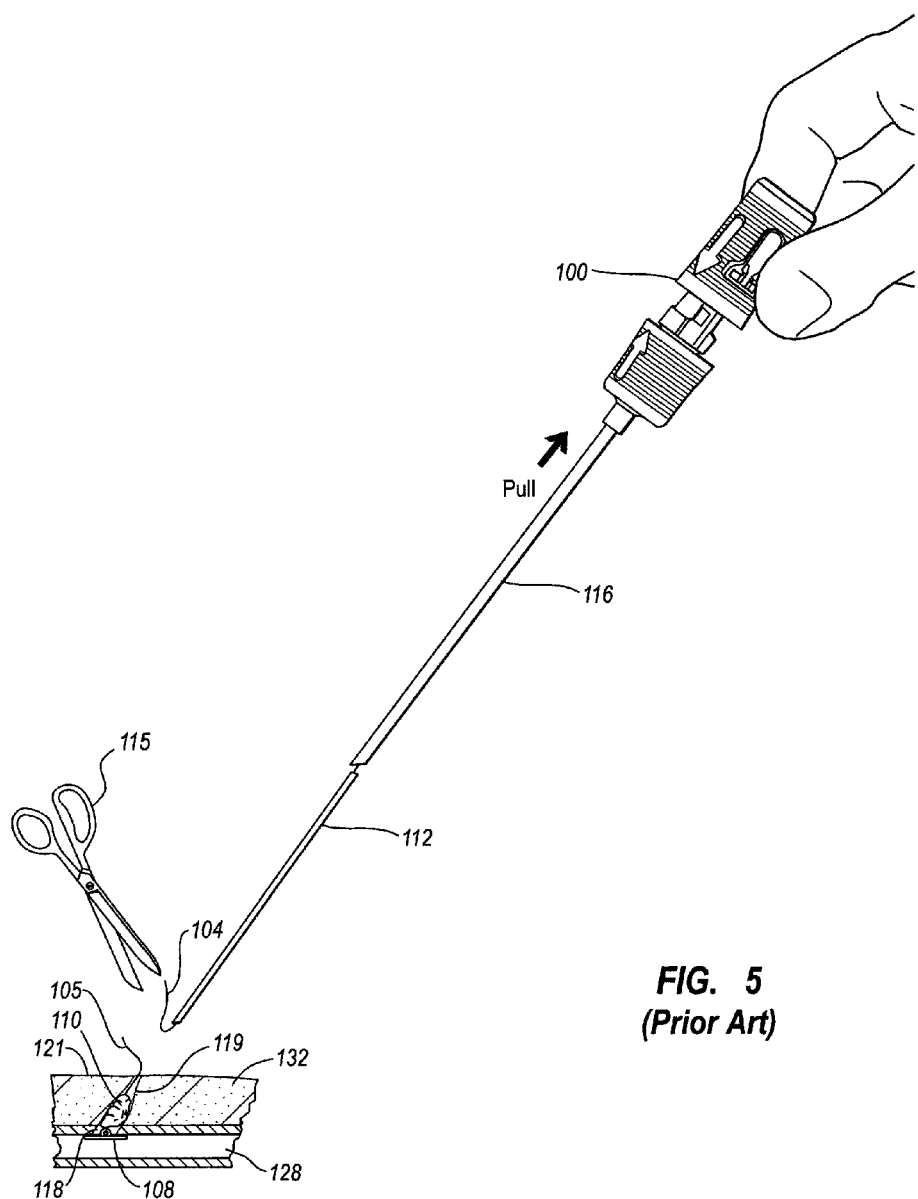
FIG. 5 is a perspective view of the vascular closure device shown in FIG. 1 with the suture being manually cut at a location outside of the percutaneous incision.

FIG. 5 illustrates cutting of the suture 104 after compaction of the collagen pad 110 is completed. Typically, the suture 104 is cut using a cutting instrument 115 that is separate and distinct from the vascular puncture closure device 100. A free or cut end 105 of the suture 104 is located outside of the percutaneous incision 119. Thus, the suture 104 passes through an outer skin surface 121.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc. While vascular closure devices are described in detail herein, vascular closure devices are merely exemplary of the many types of tissue closure devices that may benefit from the present disclosure.

Figure 6:
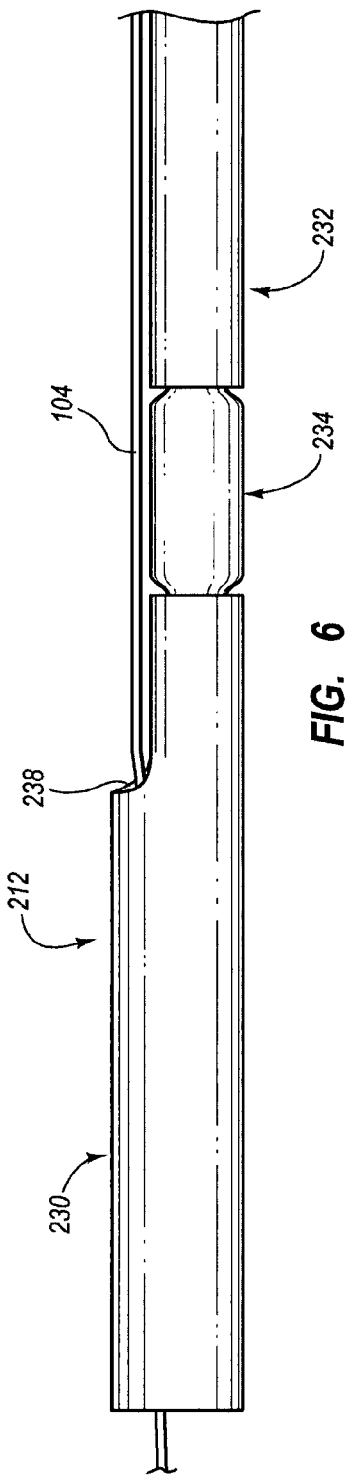
FIG. 6 is a side view of an example compaction member assembly in accordance with the present disclosure.
Figure 7:
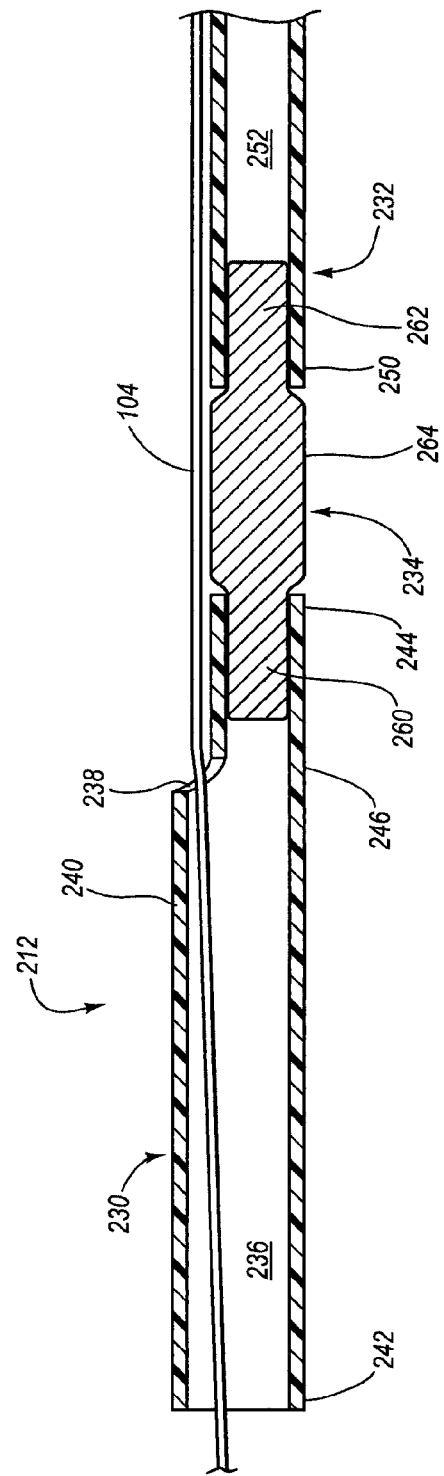
FIG. 7 is a cross-sectional view of the example compaction member assembly of FIG. 6.

Referring to FIGS. 6 and 7, an example compaction member assembly 212 includes a first portion 230, a second portion 232, and a connector 234 interposed between the first and second portions 230, 232. Typically, the first portion 230 includes a cutter aperture or a port 238 defined in the side wall 240 thereof. A suture 104 extends through the cutter aperture 238 as further discussed with reference to FIG. 8 below. A suture cutting member may be inserted through the cutter aperture 238 to cut the suture 104 at a location distal of the cutter aperture 238.

The first portion 230 includes a distal end 242, a proximal end 244, a necked-down portion 246, and a distal lumen 236. The necked-down portion 246 may be formed at least in part during the process of forming the cutter aperture 238 in the side wall 240. Some example methods of forming a cutter aperture in the resultant necked-down portion proximal of the cutter aperture are discussed below with reference to FIGS. 17-23.

The second portion 232 includes a distal end 250 and a lumen 252. The lumen 252 is sized to receive a portion of the connector 234. The distal lumen 236 of the first portion 230 is sized to receive another portion of the connector 234.

The second portion 232 may include different flexibility properties than the flexibility properties of the first portion 230. In at least one example, the second portion 232 is more flexible than the first portion 230. In at least one arrangement, a proximal end portion of the second portion 232 may have sufficient flexibility properties to permit wrapping at least a portion of the second portion 232 about a spool or other collection device that is part of a vascular closure device. An example of a vascular closure device that comprises a compaction member having a flexible portion that is wrapped or otherwise collected within a handle portion of the vascular closure device is disclosed in U.S. Pat. Nos. 7,749,248 and 7,749,247, which are hereby incorporated in their entireties by this reference.

Figure 10:
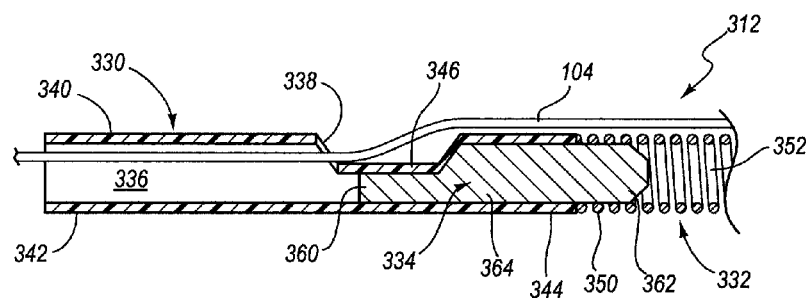
FIG. 10 is a cross-sectional view of another example compaction member assembly in accordance with the present disclosure.
Figure 13:
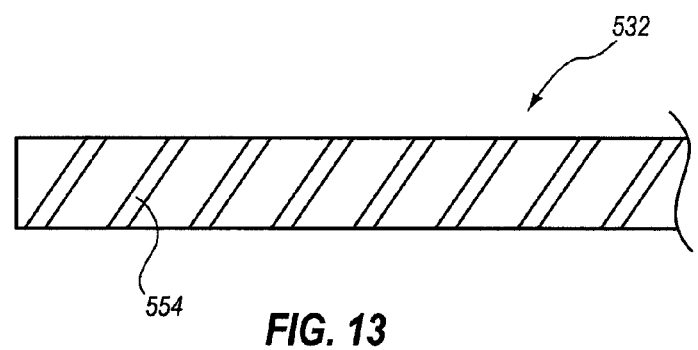
FIG. 13 is a side view of an example second portion of a compaction member assembly having a first flexible feature.

Some example constructions for a second portion that provides flexible properties are shown in FIGS. 10, and 13-15. FIG. 10 illustrates a second portion 332 that comprises a plurality of coils. In at least one example, the second portion 332 is constructed as a spring member or a member having spring-like properties. FIG. 13 illustrates a second portion 532 that includes a plurality of slits 554. The slits 554 may be arranged in a helical shape that wraps around a periphery of the second portion 532. The slits 554 may extend through an entire thickness of the side wall of the second portion. Alternatively, the slits 554 may extend through only a partial thickness of the sidewall.

Figure 14:
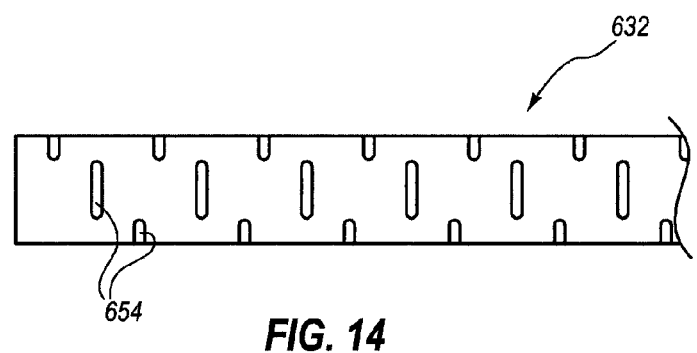
FIG. 14 is a side view of another example second portion of a compaction member assembly having a second flexible feature.

FIG. 14 illustrates a second portion 632 that includes a plurality of slits 654 that are spaced apart both axially and circumferentially around an outer surface of the second portion 632. The shape and size of the slits 654 may vary. In at least some arrangements, at least some of the slits 654 are interconnected.

Figure 15:
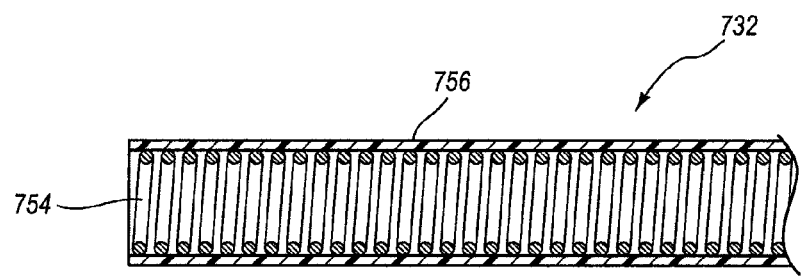
FIG. 15 is a cross-sectional view of another example second portion of a compaction member assembly having a third flexible feature.

FIG. 15 illustrates a second portion 732 having a plurality of spaces or gaps between adjacent coils 754. The second portion 732 may include a sheath or coating 756. The coating 756 may comprise, for example, a lubricious material along an outer surface thereof. The coating 756 may provide for fewer restrictions and inadvertent engagement of the coils of the second portion 732 with other features of the closure device and patient during, for example, advancing or retracting the second portion 232 into and out of a handle portion of the vascular closure device.

The connector 234 may include a distal portion 260, a proximal portion 262, and a body or middle portion 264. The distal and proximal portions 260, 262 are configured for connection to the first and second portions 230, 232, respectively. In at least one example, the distal and proximal portions 260, 262 extend into the lumens 236, 252 of the first and second portions 230, 232, respectively. Each of the distal, proximal, and body portions 260, 262, 264 may have various shapes, sizes and configurations. For example, the distal portion 260 may have a length sufficiently great that a distal portion 260 extends from the proximal end 244 distally to the cutter aperture 238 or distally beyond the cutter aperture 238. Providing an increased length for the distal portion 260 that extends into the area adjacent to the cutter aperture 238 may provide increased support for the first portion 230 that resists kinking or bending of the first portion 230 in the area of the cutter aperture 238.

The body portion 264 may have a maximum outer diameter or dimension that is no greater than a maximum outer diameter or dimension of any one of the proximal end 244, the first portion 230, and the distal end 250 of the second portion 232. Other configurations for the connector are shown in the examples that follow.

Figure 8:
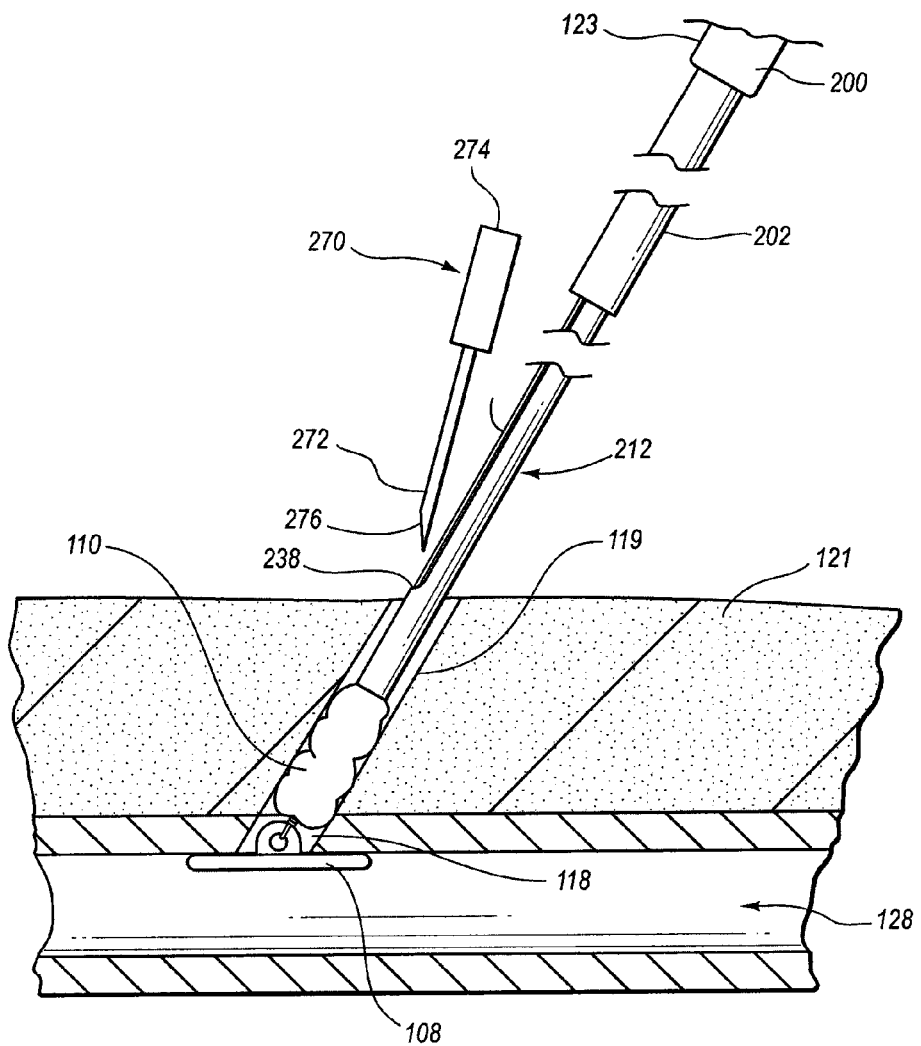
FIG. 8 is a side view of an example vascular closure device that includes the compaction member assembly of FIG. 6 positioned in a percutaneous incision and compressing a sealing pad.
Figure 9:
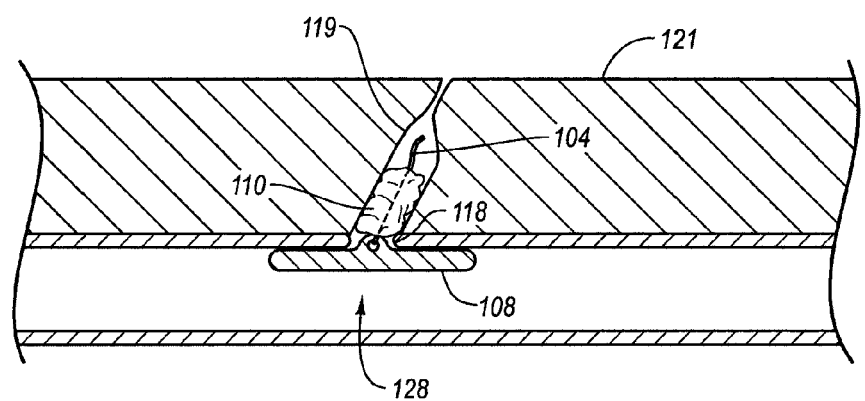
FIG. 9 is a side view showing the percutaneous incision of FIG. 8 with the suture cut below an outer surface of the skin.

Referring to FIG. 8, an example vascular closure device 200 is shown deploying a sealing plug 110 in a percutaneous incision 119 adjacent to an arterial puncture 118 in an artery 128. The vascular closure device 200 includes a carrier tube 202 extending from a housing 223. A compaction member assembly 212 extends distally from the carrier tube 202. Compaction member assembly 212 may be used to compress the sealing plug 110 toward the anchor 108 within the percutaneous incision 119. Compaction of the sealing plug 110 may be performed automatically or manually using the compaction member assembly 212. An example of manually compacting a sealing plug 110 with a compaction member is described above with reference to FIGS. 1-5. An example automatic compaction arrangement for a vascular closure device is described in, for example, U.S. Pat. No. 7,250,057, which is herein incorporated in its entirety by this reference.

As described above related to FIGS. 6 and 7, the compaction member assembly 212 includes a cutter aperture 238 located proximal of a distal end of the compaction member assembly 212. Typically, the cutter aperture 238 is exposed outside of the patient at a location above a skin surface 121. The suture 104 extends from the anchor 108, through the sealing plug 110, through an open distal end of the compaction member assembly 212, and out of the cutter aperture 238. The suture 104 typically extends proximally further into the carrier tube 202 and into the housing 223 where the suture is spooled or otherwise collected within the housing.

The vascular closure device 200 may further include a suture cutting member 270 that is configured to cut the suture at a location below the skin surface 121. The suture cutting member 270 may include a distal end 272, a handle 274, and a cutting portion 276 that is arranged at the distal end 272. The suture cutting member 270 may be held by the operator at the handle 274 and manipulated until the distal end 272 is inserted through the cutter aperture 238. The cutting portion 276 interacts with the suture 104 within the compaction member assembly 212 at a location distal of the cutter aperture 238 until the suture 104 is cut.

The suture cutting member 270 may be constructed in any of a variety of ways to provide cutting of the suture 104 within the compaction member assembly 212. For example, the suture cutting member may include a diabetic lancet construction, a hypodermic needle construction, a hot tip filament or other heat source, or a cutter construction that provides a cutting function by rotation or twisting. Some example rotation cutting devices include a drill bit, a drill buss, and a cutting disc. The suture cutting member 270 may be configured to cut the suture by longitudinal movement, lateral movement, or rotational movement relative to the suture 104. In some arrangements, at least a portion of the suture cutting member 270 at least partially extends around the suture 104 prior to and during cutting of the suture 104.

After the suture 104 is cut, the vascular closure device 200 may be removed from the patient, leaving behind the anchor 108 positioned within the artery 128 and the sealing plug 110 positioned within the percutaneous incision 119 on a side of the vessel wall opposite the anchor 108. The suture 104 may be cut at a location within the percutaneous incision 119 below the skin surface 121. As noted above, the anchor 108, sealing plug 110, and suture 104 typically comprise a bio-reabsorbable material that provides sealing of the percutaneous incision 119 and arterial puncture 118 and are later absorbed into the body.

Figure 11:
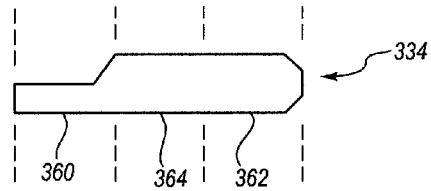
FIG. 11 is a side view of a connector of the compaction member assembly of FIG. 10.

Referring now to FIGS. 10 and 11, an alternative compaction member assembly 312 is shown and described. The compaction member assembly 312 includes a first portion 330, a second portion 332, and a connector 334. The first portion 330 includes a distal end 342, a proximal end 344, and a necked-down portion 346. A cutter aperture 338 is defined in a side wall 340 adjacent to the necked-down portion 346. The cutter aperture 338 provides an opening into a distal lumen 336 through which a suture 104 passes for exiting out of the compaction member assembly 312 at a location proximal to distal end 342.

The second portion 332 includes a distal end 350 and a lumen 352. The second portion 332 includes a plurality of slots or spaces along the length thereof. In at least one arrangement, the second portion 332 includes a plurality of coils arranged side-by-side in the configuration of a spring. The second portion 332 may have a greater flexibility property than the first portion 330.

The connector 334 includes a distal portion 360, a proximal portion 362, and a body or middle portion 364. The distal portion 360 has a reduced maximum outer dimension as compared to the outer dimension or diameter of each of the proximal and body portions 362, 364. In at least one arrangement, the distal and body portions 360, 364 are configured to extend into the distal lumen 336 with the distal portion 360 aligned radially with the necked-down portion 346 of the first portion 330. In at least some arrangements, the distal portion 360 may have a length sufficient to extend along the entire length of the necked-down portion 346. In other arrangements, the distal portion 360 may extend distally beyond the cutter aperture 338.

As noted above, the distal portion 360 may provide additional support for the first portion 330 to resist kinking or inadvertent bending of the first portion 330 in the area of the cutter aperture 338 and necked-down portion 346. The necked-down portion 346 may provide easier access to the cutter aperture 338 for passage of the suture 104 and insertion of the suture cutting member (e.g., the suture cutting member 270 described above with reference to FIG. 8).

The proximal portion 362 may be configured to extend into the lumen 352 of the second portion 332. In at least some arrangements, the proximal portion 362 may have a maximum outer dimension or diameter that is less than the maximum outer dimension or diameter of the body portion 364. The size and shape of the proximal portion 362 may be modified to fit within the lumen 352. The lumen 352 may have a different size and shape as compared to the distal lumen 336.

Figure 12:
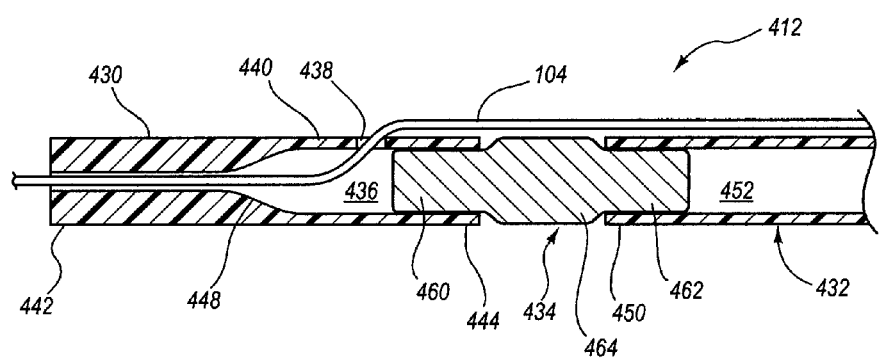
FIG. 12 is a cross-sectional view of another example compaction member assembly in accordance with the present disclosure.

Referring now to FIG. 12, another example compaction member assembly 412 is shown and described. The compaction member assembly 412 includes a first portion 430, a second portion 432, and a connector 434. The first portion 430 includes a distal end 442, a proximal end 444, a distal lumen 436, a cutter aperture 438 defined in the side wall 440, and an inner tapered portion 448. In some arrangements, the first portion 430 may also include a necked-down portion (not shown) similar to the necked-down portion 346 described above with reference to FIG. 10.

The second portion 432 includes a distal end 450 and a lumen 452. The connector 434 includes a distal portion 460, a proximal portion 462, and a body portion 464. The second portion 432 and connector 434 may have a construction and operate similar to the second portion 232 and connector 234 described above with reference to FIGS. 6 and 7.

The inner tapered portion 448 of the first portion 430 may provide for improved contact between the suture 104 and a suture cutting member that is inserted into the cutter aperture 438. In at least one example, the suture cutter member has features similar to the suture cutting member 270 described above with reference to FIG. 8, wherein a cutting portion 276 is positioned at a distal end 272 of the suture cutting member. As the distal end 272 is inserted through the cutter aperture 438 in a distal direction, and interference between the cutting portion 276 and the suture 104 begins to occur as the tapered portion narrows in the distal direction. Improving the contact between the suture cutting member and the suture 104 in a more reliable and predictable manner may improve the overall operation of the compaction member assembly 412 to cut the suture 104 at a location within the distal lumen 436.

The shape and orientation of the inner tapered portion 448 may vary to optimize operation of a particular suture cutting member that is used with the compaction member assembly 412. For example, a suture cutting member that is advanced over the suture 104 (i.e., the suture 104 passes through an aperture or opening in the suture cutting member) may optimize cutting of the suture 104 because at least partial contact between the suture 104 and suture cutting member is maintained constantly.

Figure 16:
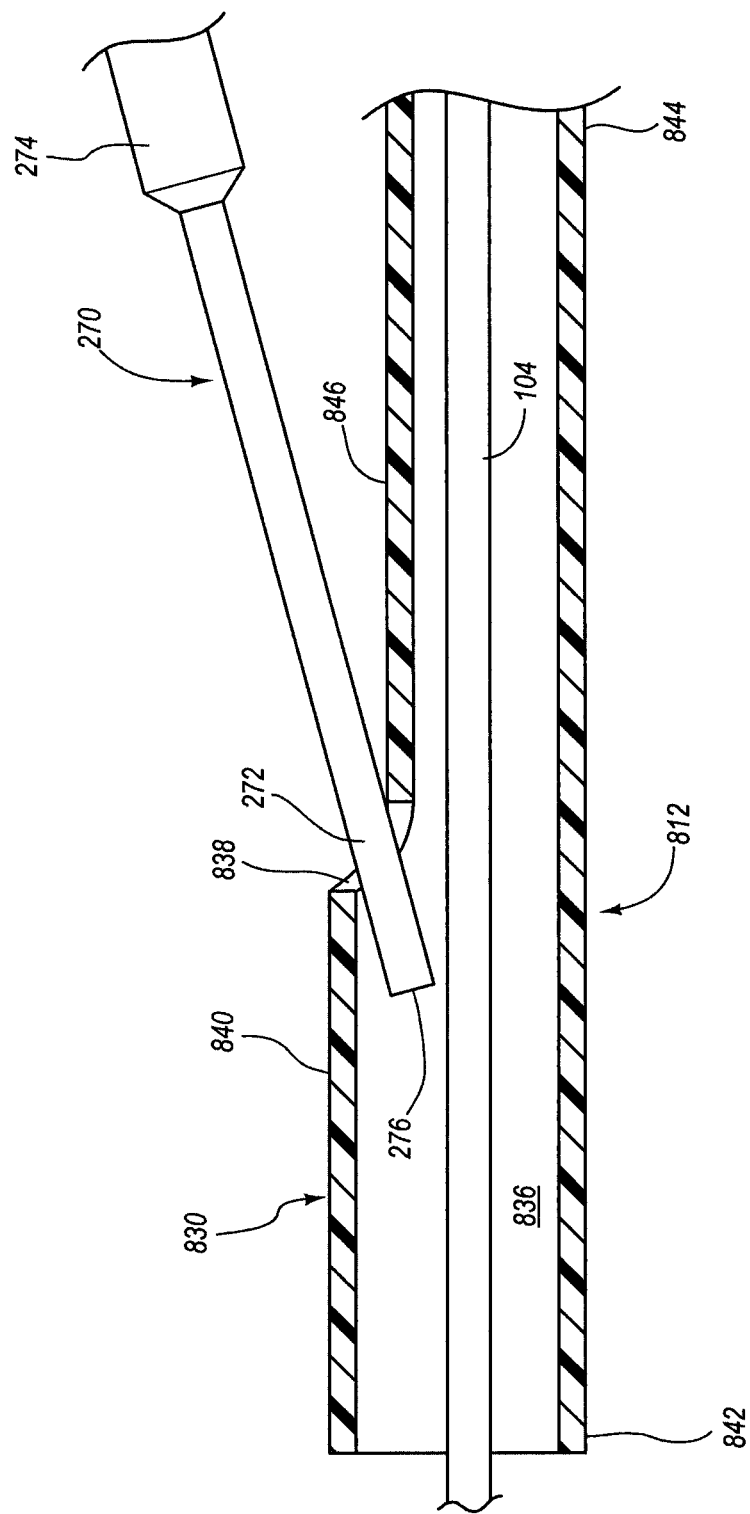
FIG. 16 is a cross-sectional view of another example compaction member assembly in accordance with the present disclosure.

Referring now to FIG. 16, another example compaction member assembly 812 is shown and described. The compaction member assembly 812 includes a single first portion 830 without use of a second portion or connector as described above with reference to compaction member assemblies 212, 312, 412. The first portion 830 includes a distal end 842, a proximal end 844, and necked-down portion 846, a distal lumen 836, and a cutter aperture 838 formed in a side wall 840. The distal end 842 is configured for insertion into a percutaneous incision and is used to compact a sealing plug. The proximal end 844 is configured to extend proximally for grasping by the operator to apply compaction force to the sealing plug, or to extend proximally into a handle portion of a vascular closure device having an automatic compaction assembly.

A suture 104 is shown extending through the distal lumen 836 from the distal end 842 proximally towards the proximal end 844 without passing through the cutter aperture 838. In other arrangements, the suture 104 may extend out of the cutter aperture 838 similar to the arrangements discussed above for compaction member assemblies 212, 312, 412.

The suture cutting member 270 may be used to cut a suture 104 within the distal lumen 836. In at least one example, the suture cutting member 270 includes a distal end 272, a handle 274 positioned proximal of a distal end 272, and a cutting portion 276 positioned at the distal end 272. Providing the compaction member assembly 812 with the necked-down portion 846 may facilitate easier insertion of the suture cutting member 270 through the cutter aperture 838 for cutting the suture 104 and provide a pathway for exit of the suture from inside the compaction member assembly 812.

The necked-down portion 846 may be formed in the compaction member assembly 812 using extrusion methods that provide the necked-down portion 846 with a smaller outer diameter or dimension than that of the distal end 842. Other methods include, for example, heat forming or heat shaping a compaction member assembly 812 to include the necked-down portion 846. An alternative to providing a necked-down portion 846 is to cut a hole in the side wall 840 using, for example, laser cutting, drilling, or heat forming the cutter aperture 838 into any desired shape or configuration.

Referring now to FIGS. 17-23, an example method of forming the compaction member assembly 912 (see FIG. 23) having a cutter aperture and necked-down portion similar to those features of compaction member assembly 812 is shown and described.

In an initial step, a first portion 930 is provided having a proximal end 944 and a lumen 936. A proximal end 944 may include a slanted or skived cut shape 980. Referring to FIG. 18, the proximal end 944 is flared to provide a proximal flared portion 982. The proximal flared portion 982 is provided so that multiple mandrels may be inserted as will be described below.

Referring to FIG. 19, a first mandrel 984 is inserted through the first portion 930 and out of the proximal end 944. A second mandrel 986 is inserted through the proximal end 944 into the proximal flared portion 982. FIG. 20 shows the arrangement of the mandrels 984, 986 within the first portion 930. In some arrangements, at least the second mandrel 986 includes a non-circular construction such as a crescent-shaped cross-section.

Referring to FIG. 21, a second portion 932 includes a lumen 952 and is prepared with a tab feature 988 formed therein at a distal end 950. FIG. 22 illustrates the tab 988 in cross-section.

Figure 23:
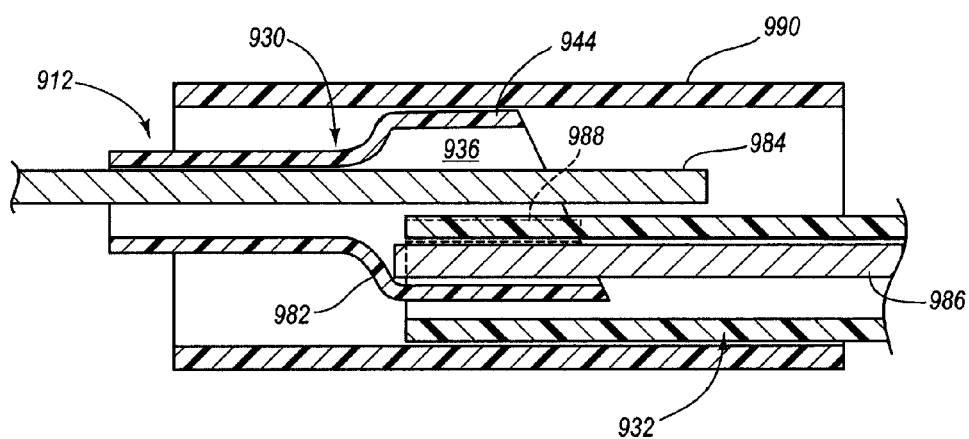
FIG. 23 is a side view of the first and second portions shown in FIGS. 19 and 21 positioned in a heat shrink sheath.
Figure 24:
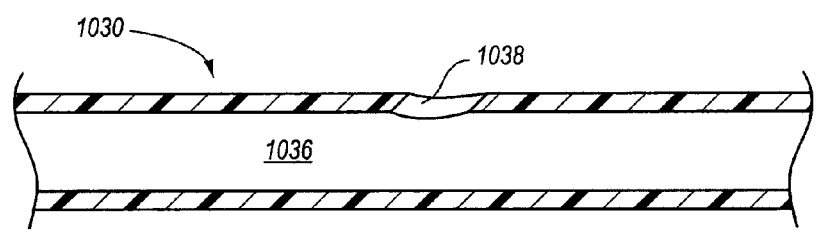
FIG. 24 is a cross-sectional view of another example compaction member assembly in accordance with principles of the present disclosure.

Referring to FIG. 23, the second portion 932 is inserted over the second mandrel 986 with the tab 988 positioned between the first and second mandrels 984, 986 and the remaining portion of the second portion 932 positioned outside of the proximal flared portion 982. In at least some arrangements, a heat shrink sheath 990 is inserted over the assembly of first and second portions 930, 932 and first and second mandrels 984, 986. A heat source is used to apply heat to the assembly shown in FIG. 23 to create a bond between the first and second portions 930, 932 with a cutter aperture being defined by the first mandrel 984. In at least some methods, the heat applied creates a material flow between the first and second portions 930, 932 so that the resulting compaction member assembly 912 is a single unitary piece.

Figure 25:
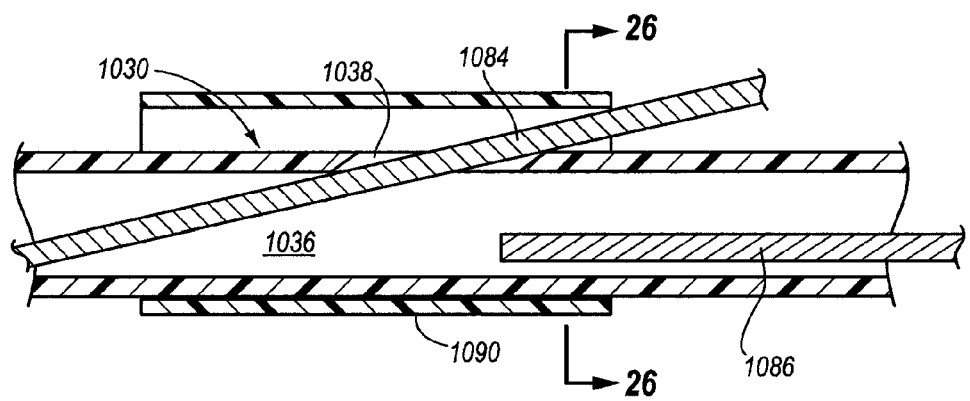
FIG. 25 is a cross-sectional view of the compaction member assembly of FIG. 24 with a pair of mandrels inserted therein.

Referring now to FIGS. 24-27, another method of defining a cutter aperture in a compaction member assembly 1012 is shown and described. A first portion 1030 of a compaction member assembly is provided with a distal lumen 1036 and a cutter aperture 1038. In at least one example, the cutter aperture 1038 is defined using, for example, laser cutting, heat forming, or drilling. A necked-down portion is defined in the first portion 1030 using, for example, a heat forming method. Referring to FIG. 25, a first mandrel 1084 is inserted through the distal lumen 1036 and out through the cutter aperture 1038. A second lumen 1086 is inserted from a proximal end within the distal lumen 1036 up to the cutter aperture 1038. A heat shrink sheath 1090 is inserted over the mandrels 1084, 1086 in the area of the cutter aperture 1038.

Figure 26:
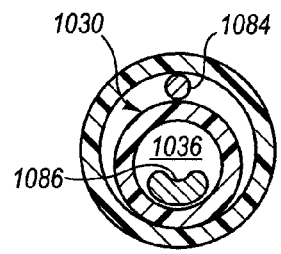
FIG. 26 is a cross-sectional view of the compaction member assembly of FIG. 25.
Figure 27:
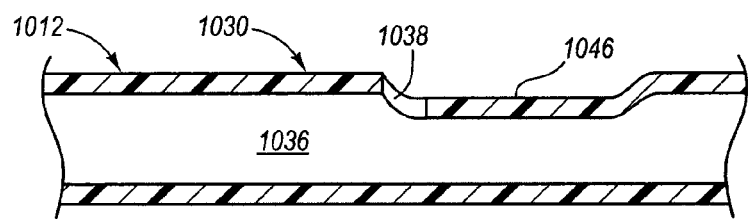
FIG. 27 is a cross-sectional view of the compaction member assembly of FIG. 25 having a necked-down portion.

FIG. 26 is a cross-sectional view showing the arrangement of the first portion 1030, first and second mandrels 1084, 1086, and heat shrink sheath 1090. A source of heat is applied to a heat shrink sheath and, in some instances, radially inward directed pressure is applied to heat and shape the first portion 1030. The resultant structure includes a necked-down portion 1046 as shown in FIG. 27.

Figure 28:
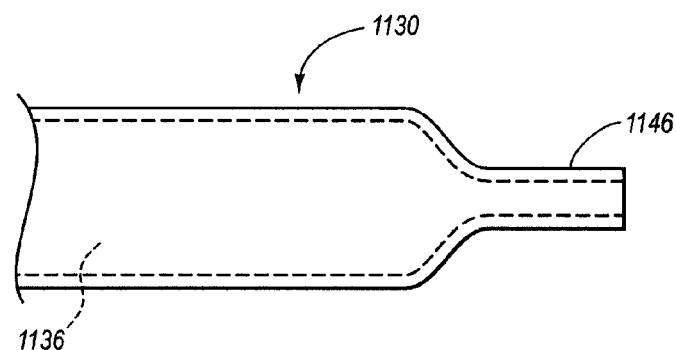
FIG. 28 is a side view of a first portion of another example compaction member assembly in accordance with the present disclosure.
Figure 29:
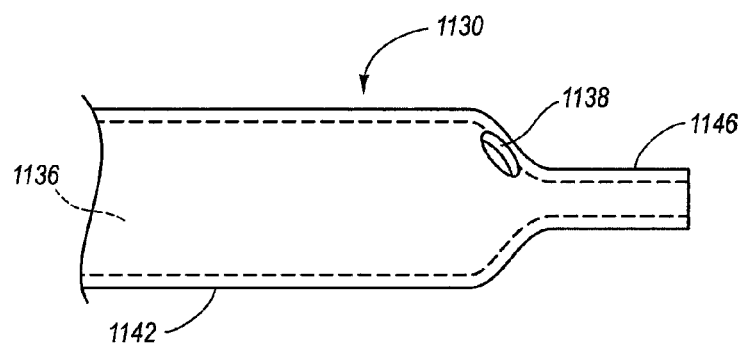
FIG. 29 is a side view of the first portion of the compaction member assembly of FIG. 28 with a port formed therein.
Figure 30:
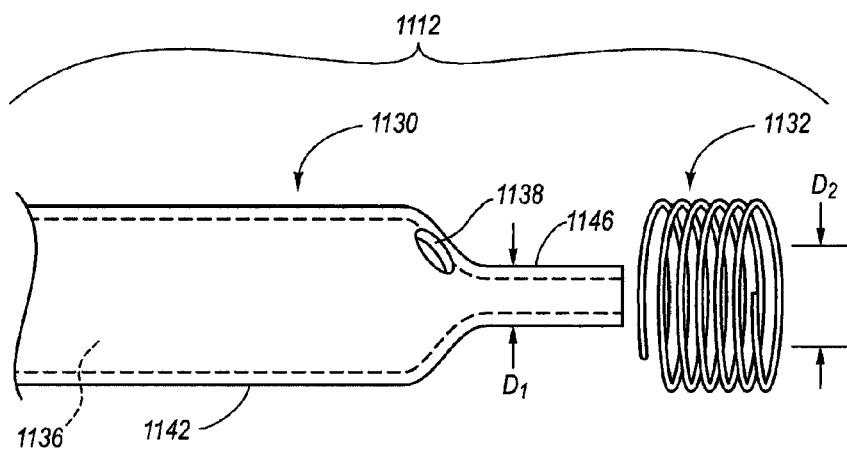
FIG. 30 is a side view of the first portion of the compaction member assembly of FIG. 29 arranged for mounting a second portion of the compaction member assembly.

Referring now to FIGS. 28-30, another example compaction member assembly 1112 is shown and described. The compaction member assembly 1112 includes a first portion 1130 having a lumen 1136 and a necked-down portion 1146 formed at a proximal end 1144. The necked-down portion 1146 may be formed in the first portion 1130 using, for example, a drawing down, necking, or heat shrinking method.

A cutter aperture 1138 may be defined in the first portion 1130 at a location adjacent to, for example, the necked-down portion 1146. In at least one example, the cutter aperture 1138 is defined in a shoulder region defined between a distal end 1142 and the necked-down portion 1146. The cutter aperture 1138 may be formed using, for example, drilling, laser cutting, or heat forming.

The necked-down portion 1146 may have a diameter $D_1$ measured at an outer surface thereof that is substantially equal to an internal diameter $D_2$ of a second portion 1132. The second portion 1132 may be sized to mount onto the necked-down portion 1146. The use of necked-down portion 1146 that is integral with the first portion 1130 may be helpful in eliminating the connector used to connect and first second portions together in the examples describe above with reference to FIGS. 6-7 and 10-12. In at least some arrangements, the first and second portions 1130, 1132 may have different flexibility properties such as, for example, the second portion 1132 having greater flexibility properties than the first portion 1130.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   an anchor;
   a sealing plug;
   a compaction member configured to move the sealing plug toward the anchor, the compaction member including a sidewall and an aperture defined in the sidewall;
   a suture coupled to the sealing plug and anchor, a portion of the suture extending through at least a portion of the compaction member and out of the aperture;
   a suture cutting member having a distal end, the distal end insertable through the sidewall and operable to cut the suture within the compaction member.

2. The tissue puncture closure device of claim 1, wherein the suture cutting member is operable to cut the suture at a location distal of the aperture.

3. The tissue puncture closure device of claim 1, wherein the suture cutting member is configured to cut the suture at a location within a percutaneous incision of a patient.

4. The tissue puncture closure device of claim 1, wherein the suture cutting member is constructed as one of a lancet, a needle, a heat cutting member, and a rotational cutting member.

5. The tissue puncture closure device of claim 1, wherein the compaction member includes a distal portion that includes the aperture, and a proximal portion coupled to a proximal end of the distal portion.

6. The tissue puncture closure device of claim 5, wherein proximal portion has a greater flexibility property than the distal portion.

7. The tissue puncture closure device of claim 5, wherein the compaction member further includes a connector configured to connect the distal portion to the proximal portion.

8. The tissue puncture closure device of claim 7, wherein a first portion of the connector is insertable into the distal portion and a second portion is insertable into the proximal portion.

9. The tissue puncture closure device of claim 1, wherein the compaction member has a greater maximum outer dimension distal of the aperture than a maximum outer dimension of the compaction member proximal of the aperture.

10. A suture cutting assembly adapted for use with a tissue puncture closure device, comprising:
   a sealing pad;
   a compaction member having an aperture defined in a sidewall thereof, the compaction member configured to compact the sealing pad;
   a suture coupled to the sealing pad;
   a suture cutting member having a distal end, the distal end adapted to extend through the sidewall and cut the suture at a location within the compaction member.

11. The suture cutting assembly of claim 10, wherein the compaction member includes a distal compaction portion having the aperture defined therein, and a proximal compaction portion connected to the distal compaction portion.

12. The suture cutting assembly of claim 11, wherein the proximal compaction portion has a greater flexibility property than the distal compaction portion.

13. The suture cutting assembly of claim 11, further comprising a connector configured to connect the distal and proximal compaction portions together at a location proximal of the aperture.

14. The suture cutting assembly of claim 10, wherein the aperture faces in an axial direction and is positioned at a location between proximal and distal ends of the compaction member.

15. A method of sealing a tissue puncture in an internal tissue wall accessible through a percutaneous incision, comprising:
   providing a tissue puncture closure device having an anchor, a sealing plug, a suture coupled to the anchor and the sealing plug, a compaction member, and a suture cutting device, the compaction member including an aperture defined in a sidewall thereof;
   inserting the tissue puncture closure device into the percutaneous incision;
   advancing the anchor through the tissue puncture;
   compressing the sealing plug within the percutaneous incision;
   extending the suture cutting device through the sidewall to cut the suture at a location within the percutaneous incision.

16. The method of claim 15, wherein the compaction member includes a distal portion and a proximal portion having different flexibility properties, and cutting the suture includes moving the suture cutting device within the distal portion.

17. The method of claim 15, further comprising extending a portion of the suture out of the aperture prior to cutting the suture.

18. The method of claim 15, wherein the tissue puncture closure device further includes a carrier tube within which the sealing plug and compaction member are positioned, wherein inserting the tissue puncture closure device includes inserting a distal end of the carrier tube into the percutaneous incision, the method further comprising retracting the carrier tube after advancing the anchor through the tissue puncture and prior to compacting the sealing plug within the percutaneous incision.

* * * * *